United States Patent [19]
Wood

[11] Patent Number: 4,783,647
[45] Date of Patent: Nov. 8, 1988

[54] SHEET MATERIAL MANUFACTURING
[75] Inventor: David F. Wood, Acton, Mass.
[73] Assignee: Aeonic Systems, Inc., Billerica, Mass.
[21] Appl. No.: 811,888
[22] Filed: Dec. 20, 1985
[51] Int. Cl.$^4$ .............................................. G08B 21/00
[52] U.S. Cl. ........................................ 340/675; 374/7
[58] Field of Search .................... 340/675; 200/61.16; 19/0.23; 250/559, 563, 238; 356/429, 431, 381–382, 384–387; 374/7, 124, 130–131, 137, 161

[56] References Cited
U.S. PATENT DOCUMENTS
3,756,524  9/1973  Felix ............................... 340/675 X OTHER PUBLICATIONS
"Motion Detection", Western Electric Tehnical Digest, No. 16, Oct. 1969.
Commercial Brochure and Technical Note for Temperature Sensor Mfd. by Measurex Corp., 1985.

Primary Examiner—Glen R. Swann, III
Assistant Examiner—Thomas J. Mullen, Jr.
Attorney, Agent, or Firm—Hale and Dorr

[57] ABSTRACT

A scanning system including a source mounted on one side of a moving web and a detector on the other, and means for monitoring changes in the air temperature in the air gaps between the moving web and, respectively, the sensor and detector. The monitoring means comprises a thin sheet of a relatively opaque and inert material having a low thermal capacity and a low thermal conductivity, mounted closely adjacent one of the gaps and a thermopile mounted on the side of the sheet away from the gap for sensing the temperature of the sheet.

In preferred embodiments in which the sheet is black polyester (e.g., "Mylar"), a sheet and thermopile are mounted on each of the sensor and detector housings, each sheet is mounted essentially coplanar with the inner side of the guide plate defining a respective air gap, and the respective thermopile is mounted on the side of its associated sheet opposite the gap.

14 Claims, 2 Drawing Sheets

SHEET MATERIAL MANUFACTURING

FIELD OF INVENTION

This invention relates to systems used in the manufacture of sheet materials such as paper and plastic and, more particularly, to systems for monitoring the thickness thereof.

BACKGROUND OF INVENTION

In the manufacture of sheet materials, at speeds up to 3000 feet per minute in the case of paper and typically 500 to 1000 feet per minute in many plastics manufacturing procedures, the thickness of the sheet material being produced is of critical importance. In the past, many different approaches have been used to monitor sheet thickness.

One such approach has been to provide scanning devices that repeatedly traverses back and forth across the rapidly moving web of sheet material being produced. Such scanning devices may include a radiation source (e.g., krypton or strontium) mounted below the web and a detector (e.g., an ion chamber) mounted above the web to measure the radiation that passes from the source and upwardly through the web. Such devices are sensitive to the total mass between the source and detector; and the detector output thus is dependent not only on the thickness (and composition) of the web but also on air in the various gaps. In many applications, particularly when thin webs are involved, the effect of the air on the total radiation passing from the source to the detector may be as great, or greater, than that of the web whose thickness is to be monitored. Further, the effect of the air is highly dependent on air temperature, and the temperature of the air in the gaps on either side of the web may change rapidly.

Typical prior efforts to account for changes in the air temperature have involved the use of thermistors to monitor the air temperature in the various gaps. These efforts have not been entirely satisfactory, particularly for the air gaps on either side of the web. In these gaps the air temperature may rapidly change, but the time constant of the thermistors is typically about 10 seconds. Further, the thermistors are usually mounted in such a way that, unless some additional mechanism is introduced to insure air flow, the air in the region surrounding the thermistors may circulate poorly.

SUMMARY OF THE INVENTION

The present invention provides a system which has a short time constant and which, essentially independently of the rest of the environment, accurately measures changes in the temperature of the air in the gaps on either side of the web without requiring moving the air around the sensor.

The invention features, in a scanning system including a source mounted on one side of a moving web, a detector on the other, and means for monitoring changes in the temperature of the air in the various air gaps between the sensor and detector, that improvement wherein the means for monitoring the temperature of air in the gaps on either side of and adjacent the web means comprises a thin sheet of a relatively opaque and inert material having a low thermal capacity and a lo thermal conductivity mounted closely adjacent one of the gaps and an infrared detector (e.g., a thermopile) mounted on the side of the target away from the gap for monitoring changes in the temperature of the thin sheet.

In preferred embodiments in which the material is black polyester (e.g., "Mylar"), such a monitoring means is mounted adjacent each of the source and detector, the thin sheet of each monitor essentially coplanar with the inner side of the guide plate defining a respective air gap, and the respective thermopile is mounted on the side of its associated thin sheet opposite the gap.

DETAILED DESCRIPTION OF PREFERRED EMBODIMENT

Figure 1:
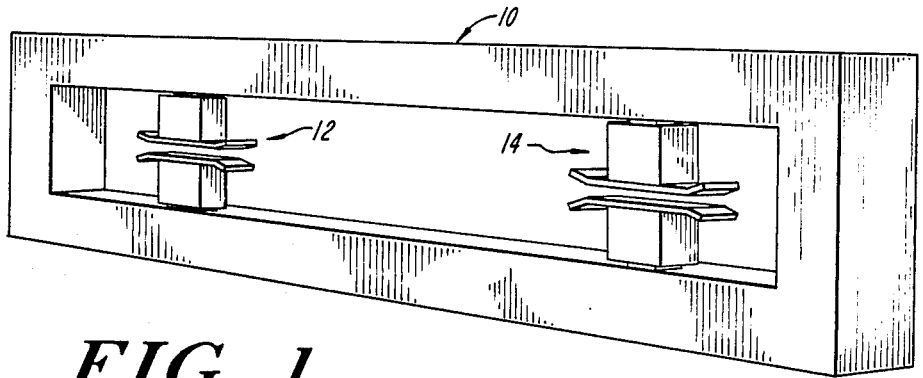
FIG. 1 is a simplified perspective view of a scanning system embodying the present invention.

Referring now to FIG. 1, there is illustrated a scanner frame, generally designated 10, on which are mounted two sensor assemblies, designated 12 and 14 respectively for measuring the thickness of a moving web 16 (shown in FIG. 1). Sensor assemblies 12 and 14 are identical to each other and only assembly 12 will be hereinafter described in detail. As shown, each sensor assembly is mounted for scanning back and forth across the width of the web 16. In practice, only one sensor assembly is used at any one time; the other provides redundancy in case of failure.

Figure 2:
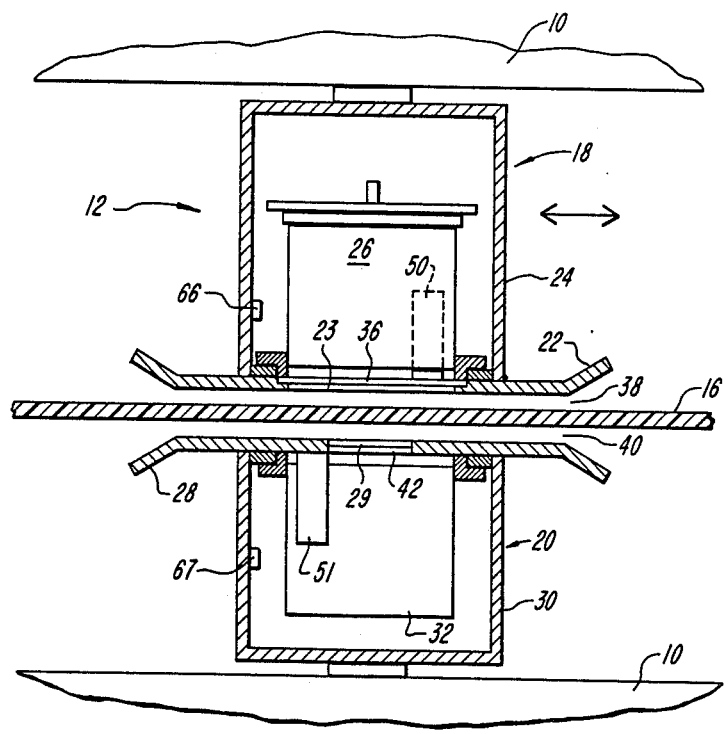
FIG. 2 is a plan view, partially in section, of portions of the system of FIG. 1.

As shown most clearly in FIG. 2, sensor assembly 12 includes a detector assembly 18 mounted above, and a source assembly 20 mounted below, web 16. The detector and source assemblies are vertically aligned witheach other, and scan back and forth across the web together while remaining in alignment.

Detector assembly 18 comprises a mounting plate 22 (including a central circular window) on and above which is supported a housing 24 containing an ion chamber 26. Source assembly 20 similarly includes a mounting plate 28 (defining a slightly smaller central circular window 29) on and below which is supported a housing 30 including radiation source chamber 32 including a source of radioactive material (typically krypton or strontium). The use of such radioactive materials, and of ion chambers responsive thereto, in scanning systems of the same general type as that used in the present invention is previously known to those working in the field.

As will be evident, there are a total of four (4) air gaps, designated 36, 38, 40 and 42, between radiation source chamber and ion chamber 26. Gaps 36 and 42 are, respectively, within the housings 24 and 30 of the detector and scanner assemblies; gaps 38 and 40 are, respectively, between detector assembly 18 and the top of web 16, and between the bottom of web 16 and source assembly 20. Typically, the total distance between detector assembly 18 and source assembly is about 0.65 in.; and, if the web 16 (typically about 0.010 in. thick) is centered between the two assemblies, the height of each of gaps 38 and 40 is about 0.32 in.

Figure 3:
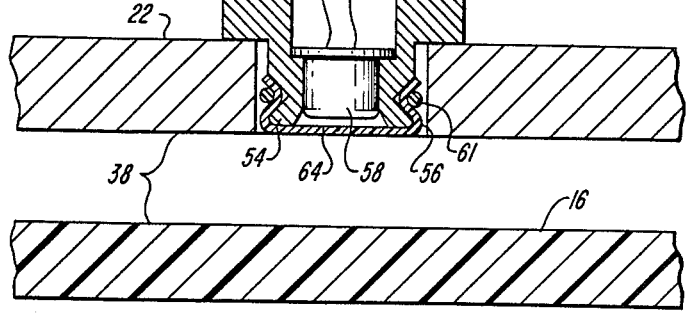
FIG. 3 is a sectional view of a portion of a detector assembly of the system of FIG. 1.

Referring now to FIG. 3, a sensor assembly 50 is mounted on support plate 22 detector assembly 18 (within housing 24) for monitoring changes in the temperature of air in gap 38. An identical sensor assembly 51 is mounted on plate 28 of source assembly 20 (within housing 30) for sensing changes in the temperature of air in gap 40. Sensor assembly 50 comprises an aluminum temperature compensating body 52 mounted on top of detector mounting plate 22 with the cylindrical head 54 of body 52 extending downwardly through a circular hole 56 in plate 22. As indicated, the relative dimensions are such that the bottom of head 54 is essentially flush with the underside of detector mounting plate 22 and there is a loose fit between the sides of head 54 and the walls of hole 56.

A thermopile detector 58 (in the illustrated embodiment a Model 2M miniature multijunction thermopile made of evaporated bismuth and antimony, having a germanium window, and sold by Dexter Research Center of Dexter, Mich.) is mounted in body 54 with the annular rim at the top of detector 58 engaging an annular step at the top of head 54 and its germanium window facing towards web 16. The thermopile detectors leads 60 extend upwardly through body 54 to a printed circuit board 62. A thin black polyester ("Mylar") sheet is wrapped around body 54, and held in place by an O-ring 61, to form a window 64 that covers the opening at the bottom of body 54, and is spaced slightly (e.g., about 0.05 in.) below thermopile detector 58. The sheet forming the window should be relatively thin so that it has a low total heat capacity and time constant; on the other hand, too thin a sheet may have inadequate strength. The black polyester used in the preferred embodiment is about 1 mil (0.001 in.) thick.

Figure 4:
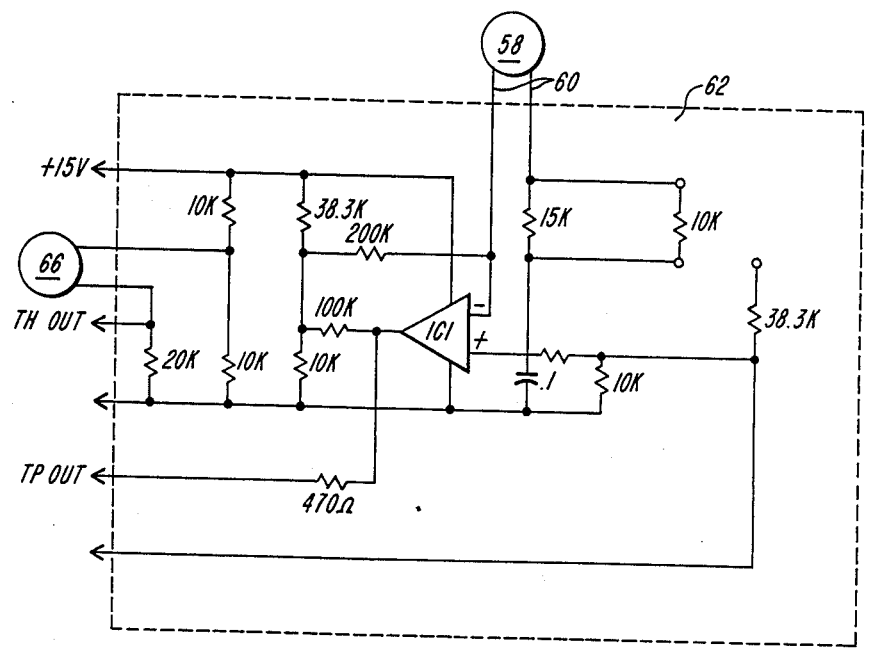
FIG. 4 is a schematic of circuitry used in the system of FIG. 1.

Referring now to FIG. 4, circuit board 62 is connected not only to thermopile detector 58, but also to a thermistor, generally designated 66, mounted in the conventional manner within the housing 24 of detector assembly 18 in position to be responsive to the temperature of air in housing 24, which in typical operation is the same as that in gap 36. Thermistor 67 is similarly mounted in the housing 30 of source assembly 20.

Thermopile detector 58 (which is a preferred type of infrared detector) monitors changes in the temperature of window 64. In the preferred embodiment, the detector 58 senses the difference between its temperature and that of window 64. The temperature of the thermopile detector 58 is essentially the same as that sensed by thermistor 66; and the temperature of window 64 is directly related to that of the air in gap 38. Because of the low thermal conductivity and capacity of the material (in the preferred embodiment, polyester) from which the window is made, its temperature quickly adjusts to changes in the air temperature, i.e., its time constant is less than one second. Thus, the thermopile detector 58 (which itself has a time constant of less than about 0.1 second) quickly responds to changes in the temperature of the air in gap 38. The output from it (identified as "TP OUT" in FIG. 4), and the outputs from the thermopile detector of sensor assembly 51 mounted on source assembly 20 and the thermistors 66, 67 mounted in detector housing 24 and source housing 30 (the output from thermistor 66 is identified as "TH OUT" in FIG. 4) permit rapid temperature compensation of the output from ion chamber 26, and thus more accurate process control.

In other embodiments, thermopiles and windows other than those of the above described preferred embodiment may be used. Similarly, air flow past the window may be added further to decrease response time (i.e., further shorten the time constant), fiber optics may be employed between the thermopile and the window to permit remote locating of the thermopile, or, if the ends of the optical fibers are made opaque (as by painting them black) the fiber ends themselves may serve as the window in lieu of, e.g., the polyester sheet. Also other types of infrared detectors may be used.

These and other embodiments will be within the scope of the following claims.

What is claimed is:

1. In a system for monitoring the thickness of a web which includes a signal source assembly and a signal detector assembly arranged to be positioned on opposite sides of said web, the signal source and signal detector assemblies including a pair of generally parallel plates spaced apart from each other and forming a gap through which the web passes, and the system including means for monitoring the temperature of the air in gaps between the signal source and the signal detector assemblies, that improvement comprising:
    a thin sheet of material having a low thermal conductivity and a low thermal capacity mounted within or closely adjacent the gap between said web and the plate of one of the signal source and signal detector assemblies and exposed to air within said gap; and,
    means arranged for monitoring changes in the temperature of the sheet.

2. The system of claim 1 wherein said means is a thermopile spaced from said sheet, and said sheet is opaque.

3. The system of claim 1 wherein said sheet is opaque polyester.

4. The system of claim 3 wherein the thickness of said sheet is less than about 2 mils.

5. The system of claim 1 wherein said means includes a metal block mounted adjacent the said assembly in thermal contact with a thermopile.

6. The system of claim 1 including a block mounted on the said plate of said assembly and defining at least part of a cavity which extends away from the web from the surface of the said plate on which said block is mounted nearest the web, and wherein said means includes a thermopile mounted in said cavity.

7. The system of claim 1 wherein said sheet is mounted essentialy coplanar with the surface of the said plate that forms part of one side of the gap between the web and said plate, and said means includes a thermopile mounted closely adjacent said sheet on the side thereof opposite said gap.

8. The system of claim 1 wherein said source assembly includes a radiation source within a source assembly housing, said detector assembly includes an ion chamber within a detector assembly housing, and including means for sensing the temperature of air within at least one of said housings.

9. The system of claim 1 wherein said means for monitoring includes a first means for sensing the temperature of air within the housing of one of said assemblies, a second means for sensing the temperature of air in the gap between the web and the plate of said one of said assemblies, and a controller for receiving the outputs from the first means and the second means.

10. The system of claim 1 including a first said means for monitoring the temperature of air in the gap between the web and the plate of one of said assemblies and a second said means for monitoring the temperature of air in the gap between the web and the plate of the other of said assemblies, said means being offset relative to each other in the direction of movement of said web and transversely of said web.

11. The system of claim 1 wherein said means is an infrared detector.

12. In a system for monitoring the thickness of a web which includes a signal source assembly and a signal detector assembly arranged to be positioned on opposite sides of said web, the signal source and signal detector assemblies including a pair of generally parallel plates spaced apart from each other and forming a gap through which the web passes, and the system including means for monitoring the temperature of the air in gap between the signal source and the signal detector assemblies, the improvement comprising:

material having a low thermal conductivity and a low thermal capacity mounted within or closely adjacent the gap between said web and the plate of one of the signal source and signal detector assemblies and defining an opaque surface exposed to air within said gap; and, means arranged for monitoring changes in the temperature of the opaque surface.

13. The system of claim 12 wherein said means is an infrared detector.

14. The system of claim 13 wherein said means is a thermopile spaced from said material.

* * * * *